United States Patent [19]

Eggers et al.

[11] Patent Number: 5,178,620

[45] Date of Patent: * Jan. 12, 1993

[54] THERMAL DILATATION CATHETER AND METHOD

[75] Inventors: Philip E. Eggers, Dublin, Ohio; Hira V. Thapliyal, Mountain View, Calif.

[73] Assignee: Advanced Angioplasty Products, Inc., Mountain View, Calif.

[*] Notice: The portion of the term of this patent subsequent to Mar. 12, 2008 has been disclaimed.

[21] Appl. No.: 660,320

[22] Filed: Feb. 22, 1991

Related U.S. Application Data

[63] Continuation-in-part of Ser. No. 204,668, Jun. 10, 1988, Pat. No. 4,998,933.

[51] Int. Cl.⁵ ............................................. A61B 17/36
[52] U.S. Cl. ..................................................... 606/41
[58] Field of Search .......................... 604/20, 96–103, 604/113, 114; 606/28, 31, 41, 194; 128/341–344, 348.1, 399–402, 786

[56] References Cited

U.S. PATENT DOCUMENTS 4,998,933 3/1991 Eggers et al. .................... 606/41

OTHER PUBLICATIONS

Dotter et al. (1964) Circulation 30:654.
Gruntzig et al. (1979) New Eng. J. Med. 301:61.
Meier and King (1984) J. Amer. College Card. 55:463.
Cumberland (Jun. 28, 1986) pp. 1457–1459.
Kensey et al. (1986) Circulation 74:(II):11.
Simpson et al. (1986) Circulation 74:(II):4 #808, 809.
Faxon et al. (1985) Circulation 72:(II):4 #1876.

*Primary Examiner*—C. Fred Rosenbaum
*Assistant Examiner*—Manuel Mendez
*Attorney, Agent, or Firm*—Townsend and Townsend

[57] ABSTRACT

This invention provides a method and an apparatus for selectively heating a resistive mass which partially or fully occludes a particular tubal passage, such as a blood vessel or the urethra. As a result, the tubal passage is effectively softened or weakened, allowing the tubal passage to be more readily recanalized by expansion of a balloon or other dilatation means. This invention also provides a method and an apparatus for effectively boring through a partially or fully occluded tubal passage by simultaneously applying both (1) heat to the occlusive mass surrounding the tip of the catheter and (2) pressure against the mass within the partially or fully occluded passage.

57 Claims, 3 Drawing Sheets

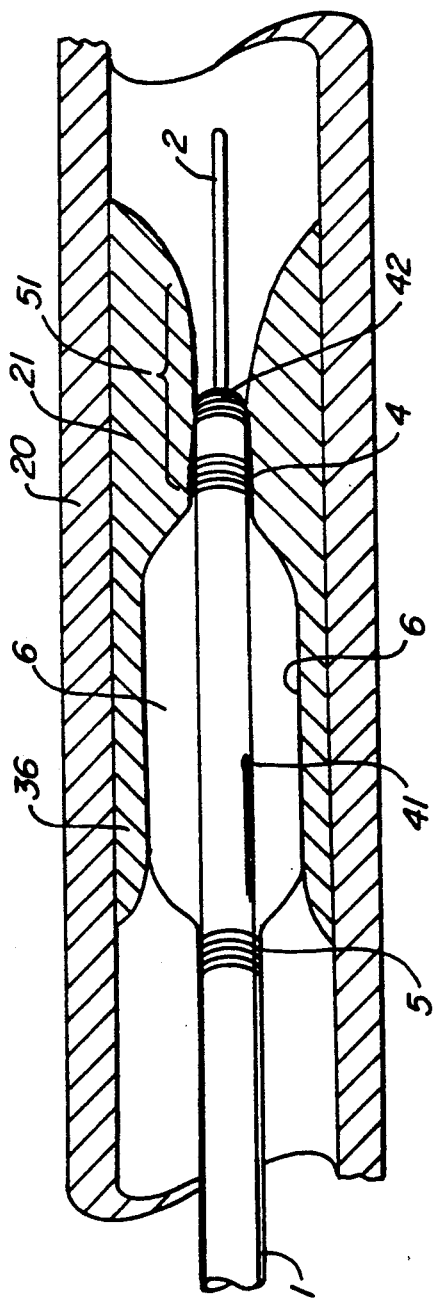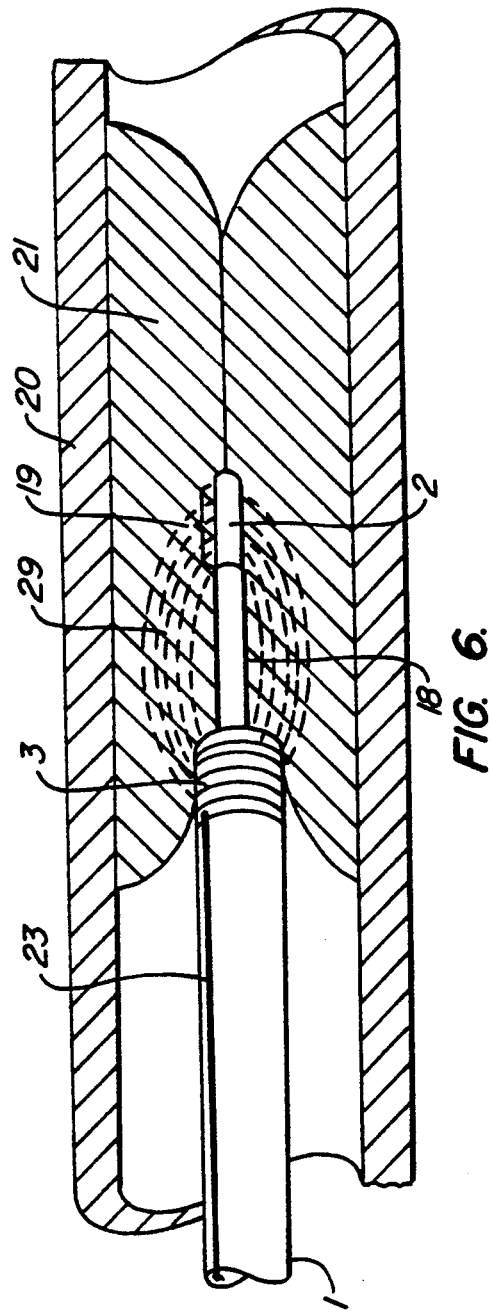

THERMAL DILATATION CATHETER AND METHOD

REFERENCE TO RELATED APPLICATION

This application is a continuation-in-part of U.S. patent application Ser. No. 204,668, filed Jun. 10, 1988, entitled "Thermal Angioplasty Catheter and Method" and now U.S. Pat. No. 4,998,933 the disclosure of which is incorporated herein by reference.

BACKGROUND OF THE INVENTION

1. Field of the Invention

This invention relates generally to catheters and in particular to a thermal dilatation catheter.

2. Description of the Prior Art

Percutaneous transluminal balloon angioplasty (PTA) has become an established technique for treating atherosclerotic occlusive disease. The principle of intraluminal dilatation of arterial plaque was described by Dotter in 1964. Dotter, C. T., et al., "Transluminal Treatment of Arteriosclerotic Obstruction: Description of a New Technique and a Preliminary Report of Its Application," Circulation (1964) 30:654. The treatment, however, was not widely accepted until the discovery of nonelastomeric balloons followed by the discovery of angiographic techniques for transluminal balloon angioplasty by Gruntzig in 1976. Gruntzig, R. A., et al., "Nonoperative Dilation of Coronary Artery Stenosis: Percutaneous Transluminal Coronary Angioplasty," New England Journal of Medicine (1979) 301:61.

The PTA technique utilizes a catheter which has a small diameter (typically 4 French to 8 French) and is equipped with an expandable chamber similar to a balloon. The chamber is concentric to the catheter and is located near the distal end of the catheter. The catheter is introduced into the appropriate blood vessel and is advanced through the vessel lumen to a narrowing of a blood vessel caused by an atheromatous mass. The deflated balloon is positioned at the site of the atheromatous plaque. The balloon is inflated in a controlled manner by injection of an appropriate fluid, compacting the atheromatous mass. After the balloon is deflated, the blood vessel has a larger luminal diameter, thereby improving blood flow.

As a result of the high percentage of initially successful dilatations, transluminal balloon angioplasty has gained widespread acceptance. However, a significant recurrence rate of 30 percent has been observed at the time of follow-up angiograms, as reported by Meier and King. Meier, B., King, S., "Repeat Coronary Angioplasty," Journal of American College of Cardiology (1984) 55:463. For this reason, other methods have been developed for the dilatation or removal of atheromatous plaque.

One method for the removal of atheromatous plaque utilizes a catheter incorporating an optical fiber for the transmission of laser energy to the distal portion of the catheter and into the stenosed arteries. Using this technique, the stenosed arteries are recanalized by the application of laser energy to ablate or vaporize the atheromatous mass. One disadvantage of this method is the widespread thermal injury to the arterial wall resulting in arterial perforation, aneurysm formation and thrombosis. Another limitation of laser ablation methods is that calcified plaques cannot be vaporized but are often fragmented by acoustic shock waves created by the pulsed laser interaction with the plaque. When such fragmentation occurs, there is an increased potential for embolization.

An alternative method for recanalization of obstructed arteries has also been developed by Spears (see European Patent No. EP-85402067) and involves the filling of the balloon (used to expand the obstructed artery) with a liquid which has a high absorbance of laser light. The laser light is then transmitted to the balloon from an external laser source via a fiber optic within the angioplasty catheter The liquid contained within the balloon is heated by the laser energy. This heating serves to minimize reclosure following conventional balloon angioplasty. Other methods of heating the fluid (e.g., water or water containing dye) in the balloon are also suggested by Spears, including exothermic (chemical) reactions and resistance heating of fluid contained within the balloon.

Another method for supplying heat to the tip of the balloon angioplasty catheter has been suggested by Cumberland, et al. Cumberland, D.C., "Percutaneous Laser Thermal Angioplasty Initial Clinical Results with a Laser Probe in Total Peripheral Artery Occlusions," Lancet (Jun. 28, 1986) pp. 1457-1459. This technique utilizes a metal tip at the distal portion of the catheter. The metal tip is heated to about 400° C. by use of an argon laser to recanalize occluded blood vessels.

Another method for recanalizing occluded blood vessels, suggested by Kensey, et al., removes atheromatous plaque by using a rotating tip catheter to "drill" or bore through the occlusive mass. Kensey, et al., "Abstracts of the 59th Scientific Sessions," Circulation (1986) 74:(II):11.

Another method of opening the stenosed blood vessel is described by Simpson, et al. Simpson J. B., et al., "Transluminal Atherectomy—Initial Clinical Results In 27 Patients," Circulation (Oct. 1986) 74 (II):4; "Transluminal Coronary Atherectomy (TCA), Results in 21 Human Cadaver Vascular Segments," Circulation (Oct. 1986) 74 (II):4; Faxon, D. P., et al., "In Vivo Evaluation of Atherectomy, A New Technique to Enlarge Atherosclerotic Vessels," Circulation (Oct 1985) 72 (II):4. In this method, a catheter device is used to cut and retrieve the occluding plaque from the artery. The catheter consists of a boat-shaped metal housing, containing a high-speed rotating cutter, and a balloon attached to the opposite side on the housing. The device is positioned at the site of the atherosclerotic narrowing in the artery, and the balloon is inflated to press the plaque into the opening of the housing. The rotating cutter is then advanced forward, thereby cutting the atheroma which is protruding into the housing The excised plaque is retrieved from the housing when the catheter is removed from the blood vessel. In this method, the lumen of the blood vessel is enlarged by cutting and removing the plaque which is occluding the blood flow. There are two main limitations of this method. First, the housing, made from a rigid material, cannot be positioned safely in blood vessels at the site of a curve, as well as at the sites of "high grade lesions" (i.e. small luminal openings). The second limitation of this device is that it removes the material in the longitudinal direction of the artery, creating a "channel" in the lumen. One has to create a number of these channels in the lumen circumferentially to more effectively treat the atherosclerotic disease in the artery.

SUMMARY OF THE INVENTION

This invention provides a method and an apparatus for selectively heating a resistive mass which partially or fully occludes a particular tubal passage, such as a blood vessel or the urethra. As a result, the occlusive mass is effectively softened or weakened, allowing the tubal passage to be more readily recanalized by expansion of a balloon or other dilatation means. This invention also provides a method and an apparatus for effectively boring through a partially or fully occluded tubal passage, such as a blood vessel or the urethra, by simultaneously applying both (1) heat to the occlusive mass surrounding the tip of the catheter and (2) pressure against the mass within the partially or fully occluded passage.

This invention includes a means for guiding the catheter and the thermal heating means along a pathway approximating the central region of the occluded tubal passage. The guiding means is an electrically conducting wire that contains or serves as the first electrode of the heating means. The guiding means is extensible from the tip of the catheter and is located within and concentric to the catheter. A second electrode is provided proximal to the first electrode and positioned on or near the tip of the catheter. The application of high frequency voltage between these two electrodes results in the conduction of high frequency current and the generation of heat within the portion of the resistive mass located between the electrodes. The application of a preselected voltage between these two electrodes for appropriate intervals of time substantially weakens the occlusive mass, allowing the catheter to penetrate and pass through the obstruction.

Once the partially or fully occluded passage has been opened to allow passage of the catheter, the catheter can be advanced to position an expansion means within the length of the occlusive mass. The expansion means is bridged by a third and a fourth electrode. These two electrodes are separated from each other by a distance of at least two catheter diameters. The expansion means is utilized for subsequent inflation and dilatation of the occlusive mass. When the third and fourth electrodes are energized by a controlled high frequency voltage level, heating occurs within the occlusive mass surrounding the expansion means. This heat weakens the mass to facilitate dilatation of the mass by the expansion means.

Direct heating of the resistive mass by conduction of a high frequency current weakens the mass over a distributed region. The use of a high frequency current for heating also minimizes induced stimulation of muscle tissue or nerve tissue in the vicinity of the tissue being heated. In addition, high frequencies minimize the risk of interfering with the natural pacing of the heart in circumstances where the thermal dilatation catheter is used to recanalize tubal passages in the heart, one of the preferred embodiments of the present invention hereinafter referred to as thermal angioplasty catheter.

In contrast, surface heating methods in which a heating element is disposed on the surface of the catheter and said heating element is heated to an elevated temperature, are limited for the following reasons. First, direct heating methods are limited by conduction heat transfer through the mass. The surface immediately adjacent to and in contact with the heating element is exposed to substantially higher temperatures than regions further away, as a consequence of the low thermal conductivity of the resistive mass. Second, direct heating methods are limited by the presence of any residue which accumulates on the surface of the heating element. The residue acts as a thermal insulating layer, impeding the transfer of heat from the heating element to the surrounding occlusive mass.

A further advantage of the present invention is that the heating means can be adapted to a wide range of catheter sizes appropriate to the particular size of the occluded tubal passage being recanalized, typically in the range of catheter diameters from 0.02 to 0.50 inches. The present invention also incorporates a guidewire which can function as both a means for controlling the path of the dilatation catheter and to concentrate the thermal power density dissipated directly into the occlusive mass by serving as the tip electrode.

The energy source of the present invention includes the capability to deliver a high frequency current at power levels ranging from several watts to 100 watts, depending on the size of the resistive mass being heated, the size of the tubal passage being recanalized, and the duration of the energy pulse being applied. The energy source allows the user to select the power level, pulse duration and number of energy pulses to be applied, according to the specific requirements of a particular dilatation procedure. The catheter of the present invention may include a temperature measuring means such that the energy source of the present invention can be controlled, in terms of applied power and/or energy pulse duration, based on the measured temperature of tissue in contact with said temperature measuring means. The temperature measurement means may be positioned on or near the tip of the catheter, on or within the guide wire, on the surface of the electrode at either side of the dilatation means, or on the surface of the dilatation means. The user also selects which region of the catheter is to be energized, depending upon the particular situation.

BRIEF DESCRIPTION OF THE DRAWINGS

FIGS. 4 and 5 are cross-sectional views of the application of a preferred embodiment of the invention to a typical vascular occlusion by using the electrodes and expansion means to heat and expand the resistive mass; and FIG. 6 is a cross-sectional view of the heating electrodes at the tip of the catheter.

DETAILED DESCRIPTION OF THE PREFERRED EMBODIMENTS

Figure 1:
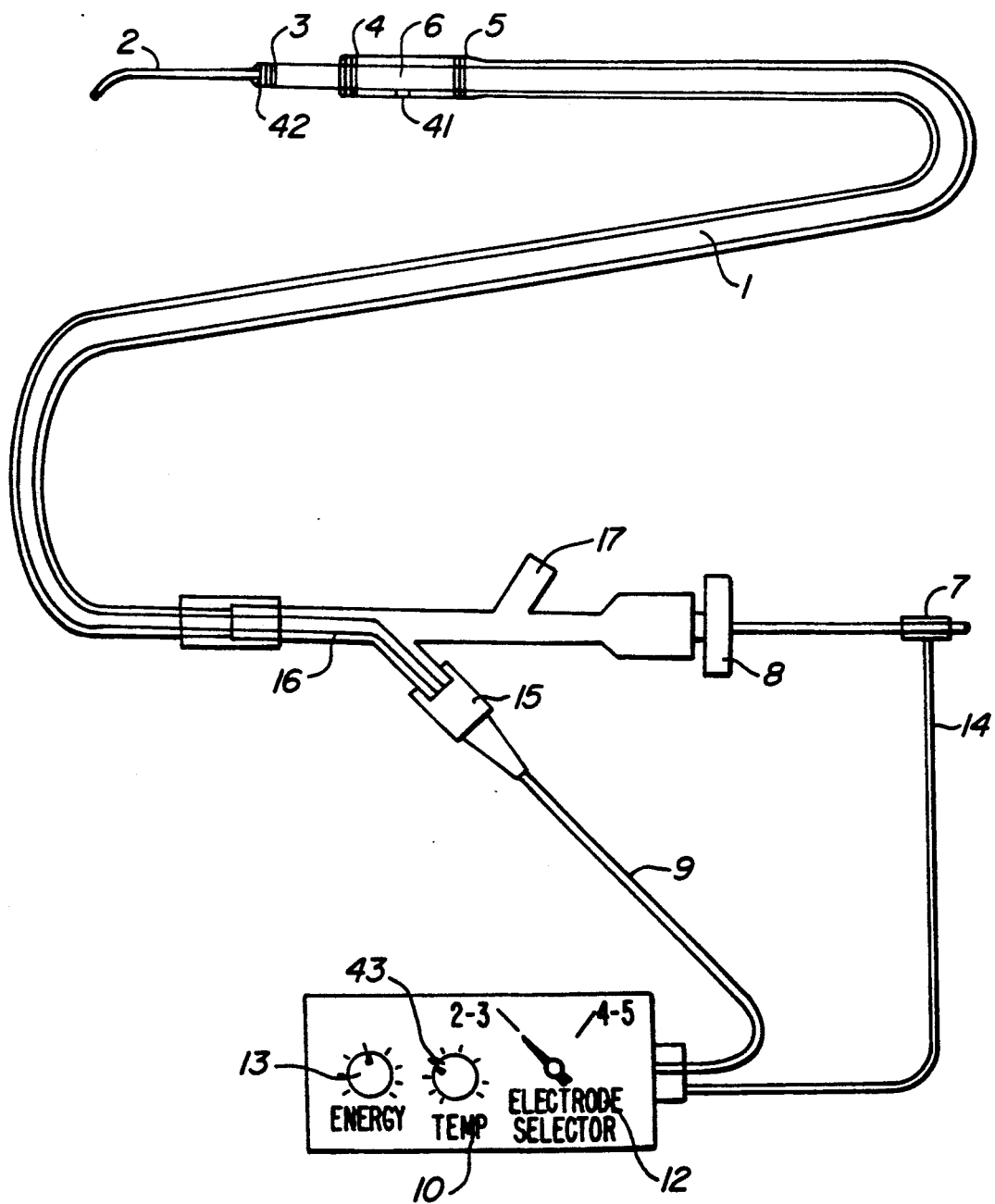
FIG. 1 is a perspective view of a thermal angioplasty catheter, which is a preferred embodiment of the thermal dilatation catheter of the present invention.

In the preferred embodiment shown in FIG. 1, the thermal angioplasty catheter 1 includes a guidewire 2, which functions both as a means for guiding the catheter into the proper position and as an electrode. The entire guidewire may be an electrode or the guidewire may contain an electrode. The catheter also includes an electrode 3, disposed on the tip of the catheter 1 and electrically insulated from and spaced by a distance of at least one catheter diameter from the guidewire electrode 2. Referring to FIG. 6, an interelectrode separation distance of at least one catheter diameter causes the current flux lines 29 in the resistive mass 21 to be distributed over the surface of electrode 3, thereby thermally weakening a portion of the resistive mass 21 which is at least as large as the diameter of electrode 3. In the preferred embodiment shown in FIG. 1, electrode 3 is hemispherical in shape with a maximum diameter substantially the same as the catheter diameter. The pair of electrodes 2 and 3 shown in FIG. 1 provides a means for applying a source of high frequency current to the resistive mass in situations in which the tubal passage is fully occluded or where the pathway is too small to allow passage of the thermal dilatation catheter 1.

Figure 4:
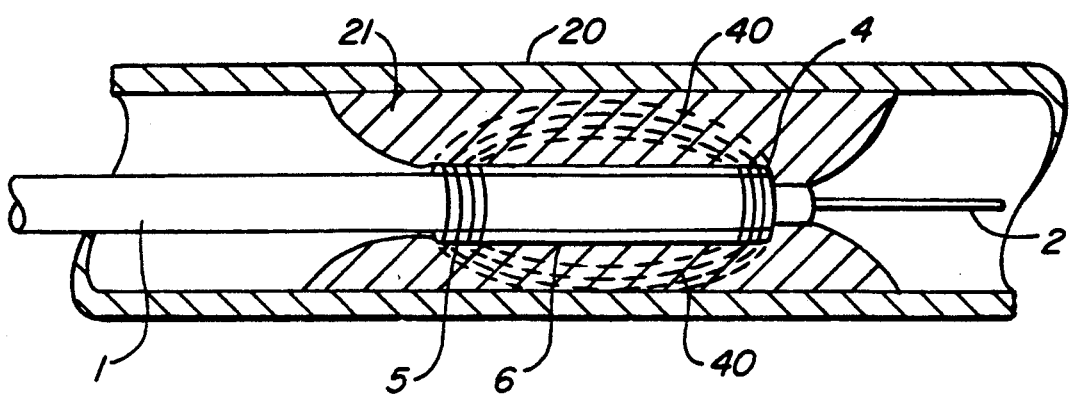

The thermal dilatation catheter 1 also includes a second set of electrodes consisting of electrode 4 and electrode 5, electrically insulated from and spaced by a distance of at least two catheter diameters from each other. Referring to FIG. 4, an inter-electrode separation distance of at least two catheter diameters causes the current flux lines 40 in the resistive mass 21 to be distributed over that portion of resistive mass 21 which is located between electrode 4 and electrode 5, said current flux lines 40 extending to radial positions larger than the radius of catheter 1, thereby thermally weakening a portion of the resistive mass 21 which is larger than the diameter of the catheter 1. Depending on the duration of the passage of current between electrodes 4 and 5 and the level of the current flux, the resistive mass 21 may be heated to temperature sufficient to cause reduction of tissue volume due to dehydration of resistive mass 21.

Referring to FIG. 1, the second set of electrodes 4 and 5 are disposed on or near the surface of the thermal dilatation catheter 1, and the outside diameter of the electrodes 4 and 5 is comparable to the diameter of the thermal dilatation catheter 1 to accommodate electrical contact with the resistive mass. Electrodes 4 and 5 are disposed near either end of an expansion means 6, which can be inflated or otherwise expanded to accomplish an increase in the inner diameter of the partially occluded tubal passage. In use, the heat provided by electrodes 4 and 5 thermally weakens the resistive mass, thereby increasing the effectiveness of the recanalization procedure. The electrodes 4 and 5 may also be disposed, in part or whole, on the surface of, and at either end of, the expansion means 6. This allows the expansion means 6, when inflated or enlarged, to ensure good electrical contact between said electrodes 4 and 5 and the resistive mass to be heated and dilated.

Referring to FIG. 1, the first set of electrodes 2 and 3 are in electrical communication with a source 10 of high frequency current through electrically conducting leads 16. The leads 16 are joined to an external cable 9 by a removable connector 15. In the embodiment of the invention shown in FIG. 1, the guidewire 2 may serve as one of the electrical leads if it is an electrically conducting material such as stainless steel. The source 10 is electrically connected to the guidewire 2 through an external lead 14 and a connector 7.

The second set of electrodes 4 and 5 are also in electrical communication with the source 10 of high frequency current through electrically conducting leads 16. The leads 16 are joined to an external cable 9 by a removable connector 15. The source 10 of high frequency current includes a means 13 for controlling the amount of energy applied to either set of electrodes 2 and 3, or 4 and 5. The source 10 of high frequency current also includes a control 12 for selecting which set of electrodes 2 and 3, or 4 and 5, is energized.

In the embodiment shown in FIG. 1, the expansion means 6 may be activated by use of a pressurizing fluid introduced in a controlled manner through external fluid port 17. The position of said guidewire 2 relative to catheter 1 may be secured by use of manually actuated locking means 8.

Figure 2:
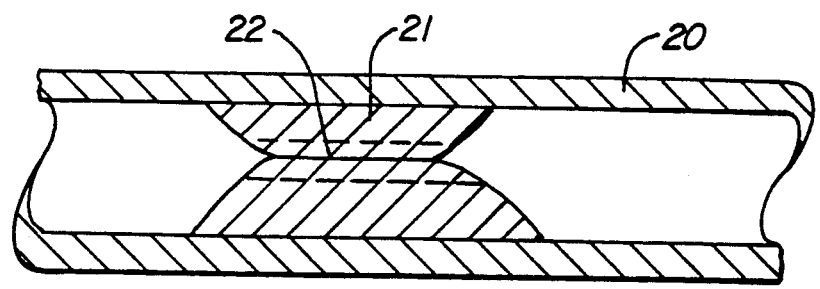
FIG. 2 is a cross-sectional view of a typical vascular occlusion prior to the recanalization.
Figure 3:
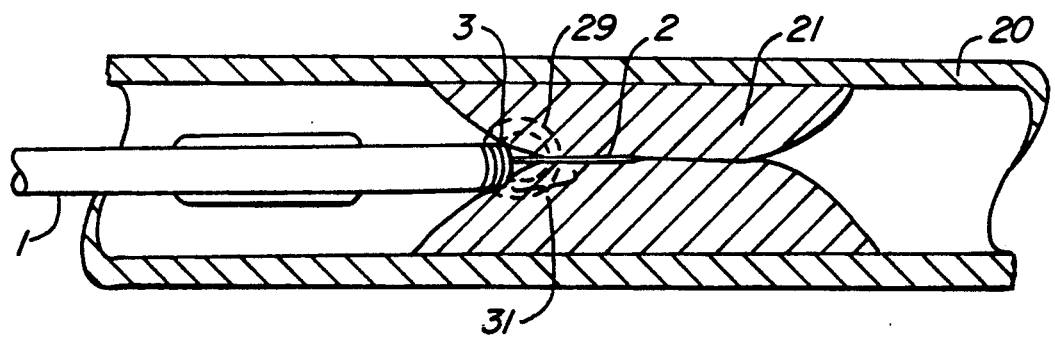
FIG. 3 is a cross-sectional view of the application of a preferred embodiment of the invention to a vascular occlusion by using the tip electrodes to penetrate through the resistive mass.

To facilitate the description of a preferred embodiment of this invention, a cross-sectional view of an occluded tubal passage is illustrated in FIG. 2. In the most severe cases of occluded tubal passages (also known as total occlusions), the tubal passage 20 is totally occluded by a resistive mass 21. In less severe cases of occluded tubal passages, also known as partially occluded tubal passages, the central region 22 of the resistive mass 21 is open, allowing a limited flow of blood FIG. 3 illustrates how the preferred embodiment of the invention can be applied to tubal passages partially or totally occluded with a resistive mass 21. In this case, the guidewire 2 is advanced to the site of the occlusion 21, then the catheter 1 is advanced along the guidewire 2 until it reaches the site of the occlusion 21. Next, the guidewire 2 is advanced beyond the tip of the catheter 1 to provide an exposed length 31 of the guidewire 2. This extension 31 of the guidewire 2 may be maintained by an enlarged guidewire diameter or mechanical "stop" which serves to prevent the guidewire 2 from completely receding into the catheter 1 while assuring a minimum exposed length 31 of guidewire 2 beyond the catheter 1.

Referring to FIG. 3, once the catheter 1 and the guidewire 2 are in contact with the resistive mass 21 at the site of the occlusion, the two electrodes 2 and 3 are energized, causing current to flow between electrodes 2 and 3 along pathways or current flux lines 29. Because of the electrical resistance of the resistive mass 21, the localized current flow 29 causes the resistive mass 21 to be heated within the envelope of the current flux lines 29. The localized heating of the mass 21 is adjusted by varying the intensity and duration of the high frequency current Still referring to FIG. 3, once a sufficient temperature rise is accomplished, the mechanical strength of the resistive mass is substantially reduced in a localized region surrounding the tip of the catheter 1. This allows the catheter 1 and the guidewire 2 to be advanced incrementally through the resistive mass 21 by applying pressure on the portions of the catheter 1 and guidewire 2 external to the patient. This pressure is transmitted along the length of the catheter 1 to the tip region of the catheter to create a load or "boring pressure" sufficient to penetrate the resistive mass 21.

The method of controlling the heating by the thermal dilatation catheter of this invention can be accomplished by other means. However, it is advantageous in many applications of the present invention to control the amount of energy delivered, selected according to the approximate size of the tubal passage being recanalized For example, the recanalization of a blood vessel with an interior nominal diameter of 0.15 inch will require more energy (i.e., calories of heat input) than the recanalization of a blood vessel having a nominal inside diameter of 0.075 inches. This is due to the difference in the mass of the occlusion to be heated to the elevated temperature range required to weaken the structure of the resistive mass. Accordingly, the invention will be described as a heating means whereby the amount of the energy delivered is controlled and is preselected by the user, according to the size of the tubal passage being recanalized. Also, the temperature measurement means 41 shown in FIG. 1 may be used to control the amount of energy delivered to the resistive mass through the application of conventional temperature feedback control methods within the source 10, thereby controlling the electric current flowing between electrodes 4 and 5 when the temperature sensor 41 reaches a preselected temperature. Similarly, a temperature measuring means 42 shown in FIG. 1 may be used to control the amount of energy delivered to the resistive mass through the application of conventional temperature feedback control methods within the source 10 thereby controlling the electric current flowing between electrodes 2 and 3 when the temperature sensor 42 reaches a preselected temperature.

Although the method of dilatation used to increase the inner diameter of the lumen by compressing the resistive mass can be accomplished by other means to achieve patency of tubal passages being recanalized, it is advantageous in many applications of the present invention to utilize an expandable means disposed on the catheter between one set of electrodes located proximal to the tip of said catheter.

This invention also can be utilized for a partially occluded tubal passage in which the diameter of the pathway for fluid flow through the resistive mass 21 is smaller than the outside diameter of the catheter 1. In this situation, the invention can be used to enlarge the pathway sufficiently to allow passage of the catheter 1, thereby accommodating the subsequent dilatation of the resistive mass 21 with the combined use of heat and expansion described more fully in FIG. 4.

FIG. 4 illustrates how a second preferred embodiment of the invention can be applied to partially occluded tubal passages. In the embodiment of this invention shown in FIG. 4, the tubal passage 20 is partially occluded with a resistive mass 21, having a pathway with a diameter sufficiently large to allow the passage of the catheter 1. The catheter 1 is advanced to the site of the occlusion and is positioned, using radiographic imaging or other means, so that the electrodes 4 and 5 are located within the length of the resistive mass 21. Once the catheter 1 and, more particularly, electrodes 4 and 5 are in contact with the resistive mass 21, the two electrodes 4 and 5 are energized, causing current to flow along flux lines 40. Because of its electrical resistance, current flow 40 in the mass 21 heats the mass 21 in the region defined within the envelope of the current flux lines 40. Heating of the mass 21 in the vicinity of electrodes 4 and 5 may be varied by adjusting the intensity and duration of current flow. The expansion means 6 is then inflated with fluid, compressing the weakened resistive mass. The expansion means is designed to withstand the application of up to 12 atmospheres of pressure. In addition, the expansion means must be able to withstand the exposure to the heated resistive mass. Following the dilatation of a region of resistive mass 21, the catheter 1 may be repositioned so that the remaining portions of the occluded tubal passage can be heated and simultaneously dilated to restore the patency of the tubal passage 20.

The embodiment of the present invention illustrated in FIG. 4 differs from that illustrated in FIG. 1 in that only three electrodes and associated leads are required in place of the four electrodes illustrated in FIG. 1. The three-electrode embodiment allows the tip electrode 4 to be used either with the proximal electrode 5 or in conjunction with the guidewire/electrode 2.

FIG. 5 illustrates how the present invention is used to expand a portion 36 of the resistive mass 21 immediately following heating in accordance with FIG. 4. After the resistive mass portion 36 is heated to a predetermined temperature range as measured by a temperature sensing means 41 disposed on the thermal dilatation catheter 1, the expansion means 6 is inflated. The temperature sensing may be achieved using fiber optics with infrared sensing techniques, a thermocouple, thermistor or other temperature measurement means, or the temperature of the resistive mass may be predetermined by introducing a predetermined quantity of energy in accordance with the approximate size of the tubal passage being recanalized. The inflation of the expansion means 6 compresses the heated mass 36, resulting in a localized increase in the interior diameter of the tubal passage. As shown in FIG. 5, the dilatation of the occluded tubal passage 20 may affect only a portion 36 of the total length of said resistive mass 21. Accordingly, following the heating and dilatation process, catheter 1 may be repositioned such that the electrodes 4 and 5 are on either side of the next section 51 of the resistive mass 21 to be dilated. The process of heating and dilatation can be repeated until the full length of the obstructed tubal passage 20 is dilated and patency of said tubal passage 20 is restored.

FIG. 6 further illustrates a detailed cross-sectional view of the catheter for use in the penetration of partially or fully occluded tubal passages. The distal end of catheter 1 is shown in contact with resistive mass 21 with guidewire/electrode 2 inserted into said resistive mass within blood vessel 20. A second electrode 3 is disposed at the distal end of catheter 1. Catheter 1 is composed of an insulating material so that the application of a high frequency voltage to the electrodes 2 and 3 will result in current flow lines 29 in the resistive mass 21. Guidewire/electrode 2 is covered with an electrically insulating layer 18 except for the tip region 19. The tip region allows the flow of current 29 between electrodes 2 and 3. Electrode 3 is connected to an external source of power by an electrical connection means 23. The electrical connection means is electrically insulated from guidewire/electrode 2 over the entire length of the catheter.

Referring to FIG. 1, in a preferred embodiment of the present invention, the source 10 is used to selectively energize electrodes 2 and 3 at the distal end of the catheter 1 or energize electrodes 4 and 5 located near either end of the dilatation means to provide a high-frequency electrical potential between said pairs of electrodes and through the resistive means (e.g., arthrosclerotic or prostatic tissue) located therebetween. The preferred frequency range is in the range of 20 kilohertz to 8 megahertz in order to provide a high enough frequency to minimize electrical stimulation of the tissue and reduce electrical hazards to the patient while providing a low enough frequency to enable the transmission of sufficient current levels to achieve adequate heating levels in the resistive mass (e.g., arthrosclerotic or prostatic tissue). The source of high-frequency energy may involve the application of a selected current level or selected voltage level for a predetermined duration or duration sufficient to achieve a preselected application of energy. Alternatively, the source of high-frequency energy may involve the application of a selected current or voltage level for a duration sufficient to achieve a preselected temperature level and then maintaining the preselected temperature level for a predetermined period of time.

While the above description provides a full and complete disclosure of the preferred embodiment of the invention, various modifications, alternative constructions, and equivalents may be employed. For example, the power could be communicated to the electrodes by wires embedded in the catheter wall. Also, a series of electrodes could be employed with multiple expansion means to "caterpillar" through an occluded tubal passage. Also, the temperature measurement means 41 shown in FIG. 1 may be used to control the amount of energy delivered to the resistive mass through the application of conventional temperature feedback control methods within the source 10, thereby controlling the electric current flowing between electrodes 4 and 5 when the temperature sensor 41 reaches a preselected temperature. Similarly, a temperature measuring means 42 shown in FIG. 1 may be used to control the amount of energy delivered to the resistive mass through the application of conventional temperature feedback control methods within the source 10 thereby controlling the electric current flowing between electrodes 2 and 3 when the temperature sensor 42 reaches a preselected temperature. Accordingly, the above description and illustration should not be construed as limiting the scope of the invention, which is defined by the appended claims.

What is claimed is:

1. A heatable dilatation catheter comprising
a catheter member;
dilation means affixed to the catheter member;
a guidewire extending through the catheter member;
a first electrode affixed to the guidewire;
a second electrode affixed to the catheter member, the second electrode electrically insulated from and spaced by a distance of at least one catheter diameter from the first electrode; and
means for selectively communicating an electric current to the first and the second electrodes to thereby cause heating of a resistive mass therebetween.

2. A catheter as in claim 1 wherein the first electrode comprises the guidewire itself.

3. A catheter as in claim 2 wherein the second electrode is affixed to the distal end of the catheter member.

4. A catheter as in claim 3 wherein the dilation means comprises a balloon.

5. A catheter as in claim 4 wherein the catheter member comprises a longitudinally-extending tube having the guidewire therethrough.

6. A catheter as in claim 1 further comprising:
temperature sensing means disposed proximate to the distal end of the catheter member for sensing temperature of regions surrounding the distal end.

7. A catheter as in claim 6 wherein the temperature sensing means is in communication with a proximal end of the catheter member to enable control of the electric current.

8. A catheter as in claim 1 further comprising:
a third electrode affixed to the catheter at a distal end of the dilatation means, the third electrode electrically insulated from and spaced by a distance of at least two catheter diameters from each of the first and the second electrodes;
a fourth electrode affixed to the catheter at a proximal end of the dilation means, the fourth electrode electrically insulated from and spaced by a distance of at least two catheter diameters from each of the first, second and third electrodes; and
means for selectively communicating an electric current to the third and the fourth electrodes to thereby cause heating of a resistive mass therebetween.

9. A catheter as in claim 1 wherein:
the first electrode extends annularly around a circumferential portion of the surface of the guidewire;
the second electrode extends annularly around a circumferential portion of the catheter member.

10. A catheter as in claim 8 wherein:
the third electrode extends annularly around a circumferential portion of the catheter member; and
the fourth electrode extends annularly around a circumferential portion of the catheter member.

11. A catheter as in claim 1 which is an angioplasty catheter.

12. A catheter as in claim 8 which is an angioplasty catheter.

13. A heatable dilatation catheter comprising:
at least two electrodes located on the catheter electrically insulated from each other and spaced by a distance of at least two catheter diameters;
means for selectively communicating an electric current to the electrodes to thereby cause heating of the resistive mass located between the electrodes; and
temperature-sensing means disposed proximate a distal end of the catheter for sensing temperature of the resistive mass being heated.

14. The catheter as in claim 13 wherein the temperature-sensing means is in communication with the proximal end of the catheter to enable control of the electric current.

15. The catheter as in claim 14 wherein the first electrode is affixed to the guidewire and spaced from the second electrode by a distance of at least one catheter diameter.

16. A catheter as in claim 15 which is an angioplasty catheter.

17. The catheter as in claim 15 further comprising:
a third electrode affixed to the catheter at a distal end of the dilation means, the, third electrode electrically insulated from each of the first and the second electrodes;
a fourth electrode affixed to the catheter at a proximal end of the dilation means, the fourth electrode electrically insulated from each of the first, second and third electrodes, and spaced by a distance of at least two catheter diameters from the third electrode; and
means for selectively communicating an electric current to the third and the fourth electrodes to thereby cause heating of a resistive mass therebetween 18. A catheter as in claim 17 which is an angioplasty catheter.

19. A heatable dilatation catheter comprising:
at least two electrodes located on the catheter electrically insulated from each other and spaced by a distance of at least two catheter diameters, each of the electrodes extending circumferentially in an annular band around the periphery of the catheter; and means for selectively communicating an electric current to the electrodes to thereby cause heating of a resistive mass located between the electrodes.

20. The catheter as in claim 19 further comprising: a guidewire extending through the catheter; and wherein the first electrode is affixed to the guidewire.

21. The catheter as in claim 20 further comprising temperature-sensing means disposed proximate a distal end of the catheter for sensing temperature of the resistive means being heated.

22. A catheter as in claim 21 which is an angioplasty catheter.

23. The catheter as in claim 21 further comprising:
a third electrode affixed to the catheter at a distal end of the dilation means, the third electrode electrically insulated from and spaced by a distance of at least two catheter diameters from each of the first and the second electrodes;
a fourth electrode affixed to the catheter at a proximal end of the dilation means, the fourth electrode electrically insulated from and spaced by a distance of at least two catheter diameters from each of the first, second and third electrodes; and
means for selectively communicating an electric current to the third and the fourth electrodes to thereby cause heating of a resistive mass therebetween.

24. A catheter as in claim 23 which is an angioplasty catheter.

25. A heatable dilatation catheter comprising:
a catheter member;
a dilatation means affixed to the catheter member;
a guidewire extending through the catheter member;
a first electrode affixed to the guidewire;
a second electrode affixed to the catheter member and electrically insulated from and spaced by a distance of at least one catheter diameter from the first electrode;
a third electrode affixed to the catheter member at a distal end of the dilation means, the third electrode electrically insulated from each of the first and the second electrodes;
a fourth electrode affixed to the catheter at a proximal end of the dilation means, the fourth electrode electrically insulated from each of the first, second and third electrodes, and spaced by a distance of at least two catheter diameters from the third electrode; and
means for selectively communicating an electric current to the first, second, third, and fourth electrodes to thereby cause heating of a resistive mass disposed in proximity to the electrodes.

26. A catheter as in claim 25 which is an angioplasty catheter

27. In a heatable catheter having a dilation means, the improvement comprising:
a first electrode located on an extensible guidewire;
a second electrode located at a distal end of the catheter electrically insulated from the first electrode;
a third electrode located at a distal end of the dilation means electrically insulated from the first and second electrodes;
a fourth electrode located at a proximal end of the dilation means electrically insulated from the first, second, and third electrodes;
whereby the first and second electrodes are separated by a distance of at least one catheter diameter from each other;
whereby the third and fourth electrodes are separated by a distance of at least two catheter diameters from each other;
whereby the guidewire comprises the first electrode;
whereby the second, third, and fourth electrodes are annular metallic regions having a wire extending therefrom;
means for selectively communicating an electric current to the electrodes to thereby cause heating of a resistive mass located between the electrodes;
whereby the means for communicating an electric current to the second, third, and fourth electrodes comprises at least one wire contained within the catheter; and
whereby the guidewire comprises the means for communicating an electric current to the first electrode.

28. A catheter as in claim 27 which is an angioplasty catheter.

29. A method of heating a resistive mass obstruction or portion thereof in a tubal passage, the method comprising the steps of:
positioning at least two electrodes, electrically insulated from each other and spaced by a distance of at least two estheter diameters, on either side of the obstruction or portion thereof;
conducting a high frequency current between the electrodes through the obstruction to thereby heat the obstruction to an elevated temperature;
sensing the elevated temperature; and
controlling the high frequency current to thereby control the elevated temperature.

30. The method of claim 29 whereby the step of positioning comprises positioning the two electrodes by means of a catheter.

31. The method of claim 29 wherein the resistive obstruction is an arteriosclerotic obstruction.

32. A method of dilatating a resistive mass obstruction or a portion thereof in a tubal passage, the method comprising the steps of:
positioning a first electrode, an inflatable expansion means, and a second electrode against the obstruction, the first and second electrodes being electrically insulated from each other and spaced by a distance of at least two catheter diameters;
conducting a high frequency current between the electrodes through the obstruction to thereby heat the obstruction to an elevated temperature;
sensing the elevated temperature;
controlling the high frequency current to thereby control the elevated temperature; and
inflating the expansion means against the obstruction.

33. The method of claim 32 wherein the resistive obstruction is an arteriosclerotic obstruction.

34. The method of claim 29 wherein the resistive obstruction is a prostatic obstruction.

35. The method fo claim 32 wherein the resistive obstruction is a prostatic obstruction.

36. A catheter as in claim 1 which is a prostatic dilatation catheter.

37. A catheter as in claim 15 which is a prostatic dilatation catheter.

38. A catheter as in claim 17 which is a prostatic catheter.

39. A catheter as in claim 21 which is a prostatic catheter.

40. A catheter as in claim 24 which is a prostatic catheter.

41. A catheter as in claim 25 which is a prostatic catheter.

42. A catheter as in claim 27 which is a prostatic catheter.

43. A catheter as in claim 8 in which said electrodes are positioned on the surface of and extend circumferentially around a dilatation means.

44. A catheter as in claim 13 in which said electrodes are positioned on the surface of and extend circumferentially around a dilatation means.

45. A catheter as in claim 19 in which said electrodes are positioned on the surface of and extend circumferentially around a dilatation means.

46. A catheter as in claim 25 in which said third and fourth electrodes are positioned on the surface of and extend circumferentially around a dilatation means.

47. A catheter as in claim 27 in which said third and fourth electrodes are positioned on the surface of and extend circumferentially around a dilatation means.

48. A catheter as in claim 29 in which said electrodes are positioned on the surface of and extend circumferentially around a dilatation means.

49. A catheter as in claim 32 in which said electrodes are positioned on the surface of and extend circumferentially around a dilatation means.

50. A means for selectively communicating an electric current as in claim 1 which operates at a frequency in the range from 20 kilohertz to 8 megahertz.

51. A means for selectively communicating an electric current as in claim 8 which operates at a frequency in the range from 20 kilohertz to 8 megahertz.

52. A means for selectively communicating an electric current as in claim 13 which operates at a frequency in the range from 20 kilohertz to 8 megahertz.

53. A means for selectively communicating an electric current as in claim 19 which operates at a frequency in the range from 20 kilohertz to 8 megahertz.

54. A means for selectively communicating an electric current as in claim 25 which operates at a frequency in the range from 20 kilohertz to 8 megahertz.

55. A means for selectively communicating an electric current as in claim 27 which operates at a frequency in the range from 20 kilohertz to 8 megahertz.

56. A means for selectively communicating an electric current as in claim 29 in which the operating frequency is in the range from 20 kilohertz to 8 megahertz.

57. A means for selectively communicating an electric current as in claim 34 in which the operating frequency is in the range from 20 kilohertz to 8 megahertz.

* * * * *